US012790424B2

(12) United States Patent
Kim et al.

(10) Patent No.: US 12,790,424 B2
(45) Date of Patent: Nov. 10, 2026

(54) POLYMER, PHOTORESIST COMPOSITION INCLUDING THE SAME, AND METHOD OF FORMING PATTERN USING THE PHOTORESIST COMPOSITION

(71) Applicant: Samsung Electronics Co., Ltd., Suwon-si (KR)

(72) Inventors: Minsang Kim, Suwon-si (KR); Haengdeog Koh, Suwon-si (KR); Yoonhyun Kwak, Suwon-si (KR); Chanjae Ahn, Suwon-si (KR); Jungha Chae, Suwon-si (KR); Sungwon Choi, Suwon-si (KR); Minyoung Ha, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 781 days.

(21) Appl. No.: 18/068,365

(22) Filed: Dec. 19, 2022

(65) Prior Publication Data

US 2024/0043592 A1 Feb. 8, 2024

(30) Foreign Application Priority Data

Jul. 21, 2022 (KR) ........................ 10-2022-0090610

(51) Int. Cl.

| | |
|---|---|
| ***G03F 7/038*** | (2006.01) |
| ***C07C 381/12*** | (2006.01) |
| ***C08F 212/14*** | (2006.01) |
| ***C08F 220/18*** | (2006.01) |
| ***G03F 7/039*** | (2006.01) |

(52) U.S. Cl.

CPC ...... *C08F 220/1807* (2020.02); *C07C 381/12* (2013.01); *C08F 212/24* (2020.02); *G03F 7/038* (2013.01); *G03F 7/039* (2013.01)

(58) Field of Classification Search

CPC ............. C08F 220/1807; C08F 212/24; C07C 381/12; G03F 7/038; G03F 7/039

See application file for complete search history.

(56) References Cited

U.S. PATENT DOCUMENTS

| | | | |
|---|---|---|---|
| 9,772,558 | B2 | 9/2017 | Ayothi et al. |
| 11,003,084 | B2 | 5/2021 | Lin et al. |
| 2019/0204742 | A1 | 7/2019 | Lee et al. |
| 2021/0278763 | A1 | 9/2021 | Hatakeyama et al. |
| 2023/0161245 | A1 | 5/2023 | Kim et al. |

FOREIGN PATENT DOCUMENTS

| | | | |
|---|---|---|---|
| JP | 2013125204 | A * | 6/2013 |
| KR | 10-2008264 | | 8/2019 |
| KR | 10-2021-0109454 | A | 9/2021 |
| KR | 10-2023-0077637 | A | 6/2023 |

OTHER PUBLICATIONS

Shuhui Kang et al, "Characterization of the Photoacid Diffusion Length and Reaction Kinetics in EUV Photoresists with IR Spectroscopy," Macromolecules, vol. 43, No. 9, pp. 4275-4286, Apr. 14, 2010.

* cited by examiner

*Primary Examiner* — Daborah Chacko-Davis

(74) *Attorney, Agent, or Firm* — Harness, Dickey & Pierce, P.L.C.

(57) ABSTRACT

Provided are a polymer including a repeating unit represented by Formula 1, a photoresist composition including the polymer, and a method of forming a pattern by using the photoresist composition:

Formula 1

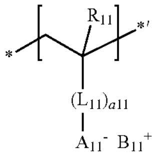

wherein the details of $R_{11}$, $L_{11}$, $a_{11}$, $A_{11}^-$, and $B_{11}^+$in Formula 1 are provided in the present specification.

20 Claims, 5 Drawing Sheets

POLYMER, PHOTORESIST COMPOSITION INCLUDING THE SAME, AND METHOD OF FORMING PATTERN USING THE PHOTORESIST COMPOSITION

CROSS-REFERENCE TO RELATED APPLICATION

This application claims the benefit of Korean Patent Application No. 10-2022-0090610, filed on Jul. 21, 2022, in the Korean Intellectual Property Office, the disclosure of which is incorporated by reference herein in its entirety.

BACKGROUND

1. Field

The disclosure relates to a polymer, a photoresist composition including the same, and a method of forming a pattern by using the photoresist composition.

2. Description of the Related Art

In manufacturing a semiconductor, photoresists (of which physical properties change in response to light) are used to form fine patterns. Among photoresists, chemically amplified photoresists have been widely used. At least one example, a chemically amplified photoresist enables patterning by changing the solubility of a base resin in a developing solution by reacting an acid, which is formed by a reaction between light and a photoacid generator, with the base resin again.

However, in the case of a chemically amplified photoresist, problems such as a decrease in pattern uniformity and/or an increase in surface roughness may be caused as the formed acid diffuses to an unexposed area. A quencher may be used to solve such problems, but the use of a quencher may cause a problem of increasing a dose required for light exposure.

Accordingly, there is a need for a quencher that may can effectively even with a small amount and has improved dispersibility and/or improved compatibility with a base resin.

SUMMARY

Provided are a polymer capable of serving as a quencher having improved dispersibility and/or improved compatibility, a photoresist composition including the polymer, and a method of forming a pattern by using the photoresist composition.

Additional aspects will be set forth in part in the description which follows and, in part, will be apparent from the description, or may be learned by practice of the presented embodiments of the disclosure.

According to an aspect of the disclosure, a polymer includes a first repeating unit represented by Formula 1:

Formula 1

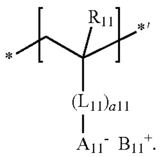

In Formula 1, $R_{11}$ may be at least one of hydrogen, a halogen, $CH_3$, $CH_2F$, $CHF_2$, or $CF_3$, $L_{11}$ may be at least one of a single bond, a substituted or unsubstituted $C_1$-$C_{10}$ alkylene group, a substituted or unsubstituted $C_3$-$C_1$ cycloalkylene group, a substituted or unsubstituted $C_1$-$C_1$ heterocycloalkylene group, a substituted or unsubstituted phenylene group, a substituted or unsubstituted naphthylene group, *—O—*', *—C(=O)O—*', —OC(=O)—*', *—C(=O)NH—*', —NHC(=O)—*', or a combination thereof, a11 may be an integer from 1 to 6, $A_{11}^-$ may be at least one of a carboxylate anion or a sulfonamide anion, $B_{11}^+$may be at least one of a substituted or unsubstituted sulfonium cation, a substituted or unsubstituted iodonium cation, or a substituted or unsubstituted ammonium cation, $A_{11}^-$ and $B_{11}^+$may be linked via at least one of an ionic bond or a carbon-carbon covalent bond, and * and *' each indicate a binding site to a neighboring atom.

According to another aspect of the disclosure, a photoresist composition includes the polymer, an organic solvent, a base resin, and a photoacid generator.

According to another aspect of the disclosure, a method of forming a pattern includes forming a photoresist film by applying the photoresist composition, exposing at least a portion of the photoresist film with high-energy rays, and developing the exposed photoresist film by applying a developing solution to the exposed photoresist film.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
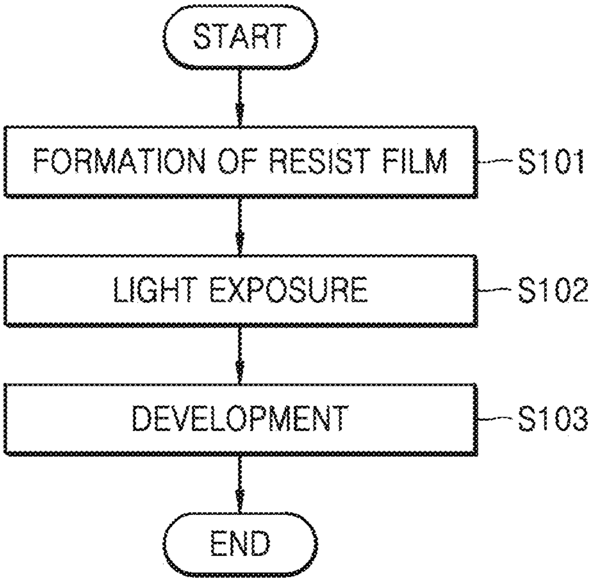
FIG. 1 is a flowchart representing a pattern forming method according to an embodiment.

Reference will now be made in detail to some example embodiments, examples of which are illustrated in the accompanying drawings, wherein like reference numerals refer to like elements throughout. In this regard, the present embodiments may have different forms and should not be construed as being limited to the descriptions set forth herein. Accordingly, the example embodiments are described below, by referring to the figure, to merely explain aspects.

As used herein, the term "and/or"includes any and all combinations of one or more of the associated listed items. Expressions such as "at least one of," when preceding a list of elements, modify the entire list of elements and do not modify the individual elements of the list.

As embodiments allows for various changes and numerous embodiments, example embodiments will be illustrated in the drawings and described in detail in the written description. However, this is not intended to limit the embodiments to particular modes of practice, and it is to be appreciated that all changes, equivalents, and substitutes that do not depart from the spirit and technical scope of the disclosure are encompassed in the embodiments. In the description of the example embodiments certain detailed explanations of the related art are omitted when it is deemed that they may unnecessarily obscure the essence of the disclosure.

Terms such as “first”, “second”, “third”, and the like may be used to describe various components but are used only for the purpose of distinguishing one component from other components, and the order, type, and/or the like of the components are not limited.

It will be understood that when a component, such as a layer, a film, a region, or a plate, is referred to as being “on” or “above” another component in the specification, the component can directly contact to be above, below, right, or left of the other component as well as being above, below, left, or right of the other component in a non-contact manner.

An expression used in the singular encompasses the expression of the plural, unless it has a clearly different meaning in the context. It is to be understood that the terms such as “including,” “having,” and “comprising” are intended to indicate the existence of the features, numbers, steps, actions, components, parts, ingredients, materials, or combinations thereof disclosed in the specification, and are not intended to preclude the possibility that one or more other features, numbers, steps, actions, components, parts, ingredients, materials, or combinations thereof may exist or may be added.

When the terms “about” or “substantially” are used in this specification in connection with a numerical value, it is intended that the associated numerical value includes a manufacturing tolerance (e.g., ±10%) around the stated numerical value. Further, regardless of whether numerical values are modified as “about” or “substantially,” it will be understood that these values should be construed as including a manufacturing or operational tolerance (e.g., ±10%) around the stated numerical values.

Whenever a range of values is enumerated, the range includes all values within the range as if recorded explicitly clearly and may further include the boundaries of the range. Accordingly, the expression in a range of “X” to “Y” includes all values between X and Y as well as X and Y.

Hereinafter, the disclosure will be described in detail by explaining embodiments with reference to the accompanying drawings, and substantially identical or corresponding components are given the same reference numerals in the drawings, and thus a description thereof will be omitted. In the drawings, thicknesses are enlarged to clearly represent various layers and regions. In the drawings, thicknesses of some layers and regions are exaggerated for convenience of description. Meanwhile, embodiments described below are illustrative examples of embodiments, and various changes in forms and details may be made.

[Polymer]

A polymer according to at least one embodiment may include a first repeating unit represented by Formula 1:

Formula 1

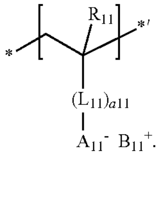

In Formula 1, $R_{11}$ may be at least one of hydrogen, a halogen, $CH_3$, $CH_2F$, $CHF_2$, and/or CF3; $L_{11}$ may be at least one of a single bond, a substituted or unsubstituted $C_1$-$C_{10}$ alkylene group, a substituted or unsubstituted $C_3$—$C_1$ cycloalkylene group, a substituted or unsubstituted $C_1$-$C_1$ heterocycloalkylene group, a substituted or unsubstituted phenylene group, a substituted or unsubstituted naphthylene group, *—O—*', *—C(═O)O—*', —OC(═O)—*', *—C(═O)NH—*', —NHC(═O)—*', or a combination thereof, a11 may be an integer from 1 to 6;$A_{11}^-$ may be at least one of a carboxylate anion or a sulfonamide anion;$B_{11}^+$may be a substituted or unsubstituted sulfonium cation, a substituted or unsubstituted iodonium cation, or a substituted or unsubstituted ammonium cation; and * and *' each indicate a binding site to a neighboring atom. In at least one embodiment, the $A_{11}^-$ and $B_{11}^+$may be linked via an ionic bond and/or a carbon-carbon covalent bond.

When $L_{11}$ in Formula 1 is a “$C_1$-$C_1$ alkylene group”, $L_{11}$ may be, e.g., one of a methylene group, an ethylene group, a propylene group, a butylene group, an isobutylene group, and/or the like.

When $L_{11}$ in Formula 1 is a “$C_3$—$C_{10}$ cycloalkylene group”, $L_{11}$ may be, e.g., one of a cyclopentylene group, a cyclohexylene group, an adamantylene group, an adamantylmethylene group, a norbornylene group, a norbornylmethylene group, a tricyclodecanylene group, a tetracyclododecanylene group, a tetracyclododecanylmethylene group, a dicyclohexylmethylene group, and/or the like.

When $L_{11}$ in Formula 1 is a “$C_1$-$C_1$ heterocycloalkylene group”, the $C_1$-$C_1$ heterocycloalkylene group may refer to a group in which some carbon atoms of the “$C_3$—$C_{10}$ cycloalkylene group” are substituted with a moiety including a heteroatom, such as oxygen, sulfur, or nitrogen. In this regard, the $L_{11}$ may include, e.g., one of an ether linkage, an ester linkage, a sulfonic ester linkage, a carbonate, a lactone ring, a sultone ring, a carboxylic anhydride moiety, and/or the like.

In Formula 1, a11 indicates the number of repetitions of $L_{11}$, wherein, when a11 is 2 or more, a plurality of $L_{11}$ may be identical to or different from each other.

In Formula 1, $A_{11}^-$ may be represented by at least one of Formula 2-1 or 2-2:

Formula 2-1

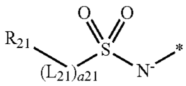

Formula 2-2

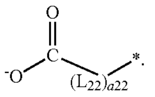

In Formulae 2-1 and 2-2, $L_{21}$ and $L_{22}$ may each independently be at least one of a single bond, a $C_1$-$C_6$ alkylene group, a $C_1$-$C_6$ alkylene group substituted with fluorine (F), and/or any combination thereof; $a_{21}$ and $a_{22}$ may each independently be an integer from 1 to 3, $R_{21}$ may be F or a linear, branched, and/or cyclic $C_1$-$C_{20}$ monovalent hydrocarbon group; and * indicates a binding site to a neighboring atom.

For example, * may represent the binding site linking between Formulae 2-1 and 2-2 and 11. At least one embodiment, the cyclic $C_1$-$C_{20}$ monovalent hydrocarbon group of $R_{21}$ may include a heteroatom.

The “$C_1$-$C_6$ alkylene group substituted with F” in Formulae 2-1 and 2-2 may be a group in which at least one of the hydrogens in the “$C_1$-$C_6$ alkylene group” is substituted with at least one F.

In Formulae 2-1 and 2-2, $a_{21}$ and $a_{22}$ indicate the number of repetitions of $L_{21}$ and the number of repetitions of $L_{22}$, respectively, wherein a plurality of $L_{21}$ may be identical to or different from each other when $a_{21}$ is 2 or more, and a plurality of $L_{22}$ may be identical to or different from each other when $a_{22}$ is 2 or more.

Regarding $R_{21}$ in Formula 2-1, the monovalent hydrocarbon group may include, for example, a linear or branched alkyl group (e.g., a methyl group, an ethyl group, a propyl group, an isopropyl group, a butyl group, an isobutyl group, a sec-butyl group, a tert-butyl group, a pentyl group, a neopentyl group, a hexyl group, a heptyl group, a 2-ethylhexyl group, a nonyl group, and/or the like); a monovalent saturated alicyclic hydrocarbon group (e.g., a cyclopentyl group, a cyclohexyl group, a cyclopentylmethyl group, a cyclopentylethyl group, a cyclopentylbutyl group, a cyclohexylmethyl group, a cyclohexylethyl group, a cyclohexylbutyl group, a 1-adamantyl group, a 2-adamantyl group, a 1-adamantylmethyl group, a norbornyl group, a norbornylmethyl group, a tricyclodecanyl group, a tetracyclododecanyl group, a tetracyclododecanylmethyl group, a dicyclohexylmethyl group, and/or the like); a monovalent unsaturated aliphatic hydrocarbon group (e.g., an allyl group, a 3-cyclohexenyl group, and/or the like); an aryl group (e.g., a phenyl group, a 1-naphthyl group, a 2-naphthyl group, and/or the like); an arylalkyl group (e.g., a benzyl group, a diphenylmethyl group, and/or the like); and/or a heteroatom-containing monovalent hydrocarbon group (e.g., a tetrahydrofuranyl group, a methoxymethyl group, an ethoxymethyl group, a methylthiomethyl group, an acetamidemethyl group, a trifluoroethyl group, a (2-methoxyethoxy)methyl group, an acetoxymethyl group, a 2-carboxy-1-cyclohexyl group, a 2-oxopropyl group, a 4-oxo-1-adamantyl group, a 3-oxocyclohexyl group, and/or the like). Also, among these groups, some hydrogen atoms may be substituted with a moiety including a heteroatom (such as oxygen, sulfur, nitrogen, a halogen atom, and/or the like) and/or some carbon atoms may be replaced by a moiety including a heteroatom (such as oxygen, sulfur, nitrogen, and/or the like). For example, these groups may include a hydroxy group, a cyano group, a carbonyl group, a carboxyl group, an ether linkage, an ester linkage, a sulfonic ester linkage, a carbonate, a lactone ring, a sultone ring, a carboxylic anhydride moiety, a haloalkyl moiety, and/or the like.

In at least one example embodiment, $R_{21}$ in Formula 2-1 may be: F or, e.g., a methyl group, an ethyl group, a propyl group, an isopropyl group, a butyl group, an isobutyl group, a sec-butyl group, a tert-butyl group, a pentyl group, a neopentyl group, a hexyl group, a heptyl group, a 2-ethylhexyl group, an n-nonyl group, a cyclopentyl group, a cyclohexyl group, a cyclopentylmethyl group, a cyclopentylethyl group, a cyclopentylbutyl group, a cyclohexylmethyl group, a cyclohexylethyl group, a cyclohexylbutyl group, a 1-adamantyl group, a 2-adamantyl group, a 1-adamantylmethyl group, a norbornyl group, a norbornylmethyl group, a tricyclodecanyl group, a tetracyclododecanyl group, a tetracyclododecanylmethyl group, a dicyclohexylmethyl group, a phenyl group (each unsubstituted or substituted with F), and/or the like.

In one or more embodiments, $R_{21}$ in Formula 2-1 may be F, $CH_2F$, $CHF_2$, or CF3.

In Formula 1, $B_{11}^{+}$may be represented by one of Formulae 3-1 to 3-3:

3-1

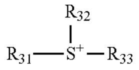

3-2

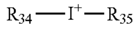

3-3

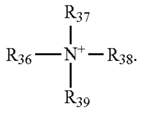

In Formulae 3-1 to 3-3, $R_{31}$ to $R_{39}$ may each independently be a linear, branched, and/or cyclic $C_1$-$C_{20}$ monovalent hydrocarbon group. In at least one embodiment, $R_{31}$ to $R_{39}$ may include a heteroatom and/or two adjacent groups among $R_{31}$ to $R_{39}$ may be bonded to each other to form a ring. For example, two adjacent groups among $R_{31}$ to $R_{33}$ may be bonded to each other to form a ring; $R_{34}$ and $R_{35}$ may be bonded to each other to form a ring; and/or two adjacent groups among $R_{36}$ to $R_{39}$ may be bonded to each other to form a ring.

The "monovalent hydrocarbon group" in Formulae 3-1 to 3-3 may be understood by referring to the case where $R_{21}$ in Formulae 2-1 and 2-2 is the "monovalent hydrocarbon group".

For example, in at least one example embodiment, in Formulae 3-1 to 3-3, $R_{31}$ to $R_{35}$ may each independently be a $C_6$—$C_{20}$ aryl group unsubstituted or substituted with at least one of a halogen, a hydroxyl group, a $C_1$-$C_6$ alkyl group, a $C_1$-$C_6$ alkoxy group, a $C_3$—$C_6$ cycloalkyl group, a $C_3$—$C_6$ cycloalkoxy group, and/or the like; $R_{36}$ to $R_{39}$ may each independently be a $C_1$-$C_1$ alkyl group unsubstituted or substituted with at least one of a halogen, a hydroxyl group, a $C_1$-$C_6$ alkyl group, a $C_1$-$C_6$ alkoxy group, a $C_3$-$C_6$ cycloalkyl group, a $C_3$—$C_6$ cycloalkoxy group, a $C_6$—$C_{10}$ aryl group, and/or the like; two adjacent groups among $R_{31}$ to $R_{33}$ may be bonded to each other to form a ring; $R_{34}$ and $R_{35}$ may be bonded to each other to form a ring; and/or two adjacent groups among $R_{36}$ to $R_{39}$ may be bonded to each other to form a ring. In Formula 1, $B_{11}^{+}$may be represented by one of Formulae 3-11 to 3-13:

3-11

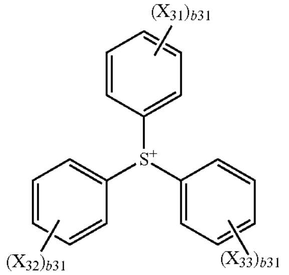

-continued 3-12

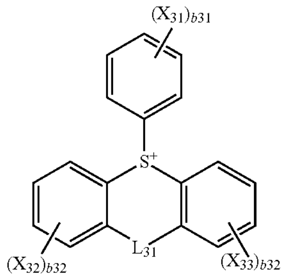

3-13

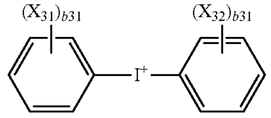

In Formulae 3-11 to 3-13, X31 to $X_{33}$ may each independently be at least one of hydrogen, a halogen, or a $C_1$-$C_6$ alkyl group; b31 may be an integer from 1 to 5; 32 may be an integer from 1 to 4; $L_{31}$ may be at least one of a single bond, O, S, CO, SO, SO2, CRR', or NR; and R and R' may each independently be at least one of hydrogen (e.g., protium and/or deuterium), a halogen, a hydroxyl group, a $C_1$-$C_6$ alkyl group, a $C_1$-$C_6$ alkoxy group, a $C_3$—$C_6$ cycloalkyl group, a $C_3$—$C_6$ cycloalkoxy group, and/or the like.

For example, $X_31$ to $X_{33}$ in Formulae 3-11 to 3-13 may each independently be hydrogen, F, or I.

In at least one embodiment, the polymer may consist of the first repeating unit, and/or may be in the form of a copolymer that additionally includes a different repeating unit.

For example, the polymer may further include a second repeating unit selected from a repeating unit represented by Formula 4 and/or a repeating unit represented by Formula 5:

Formula 4

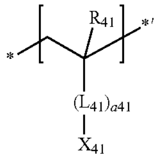

Formula 5

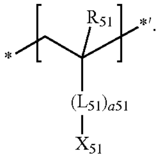

In Formulae 4 and 5, $R_{41}$ and $R_{51}$ may each independently be hydrogen, a halogen, $CH_3$, $CH_2F$, $CHF_2$, or CF3; $L_{41}$ and $L_{51}$ may each independently be a single bond, a substituted or unsubstituted $C_1$-$C_1$ alkylene group, a substituted or unsubstituted $C_3$-$C_1$ cycloalkylene group, a substituted or unsubstituted $C_3$—$C_{10}$ heterocycloalkylene group, a substituted or unsubstituted phenylene group, a substituted or unsubstituted naphthylene group, *—O—*', *—C(═O)O—*', —OC(═O)—*', *—C(═O)NH—*', —NHC(═O)—*', any combination thereof, and/or the like; a41 and a51 may each independently be an integer of 1 to 6; $X_{41}$ may be an acid labile group, and $X_{51}$ may be a non-acid labile group, and * and *' each indicate a binding site to a neighboring atom.

In Formulae 4 and 5, $L_{41}$ and $L_{51}$ may each be the same, and/or substantially similar, as described in connection with $L_{11}$ in Formula 1.

In Formulae 4 and 5, $a_{41}$ and $a_{51}$ indicate the number of repetitions of $L_{41}$ and the number of repetitions of $L_{51}$, respectively, wherein a plurality of $L_{41}$ may be identical to or different from each other when $a_{41}$ is 2 or more, and a plurality of $L_{51}$ may be identical to or different from each other when $a_{51}$ is 2 or more.

In at least one embodiment, $X_{41}$ in Formula 4 may be represented by one of Formulae 6-1 to 6-7:

6-1

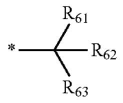

6-2

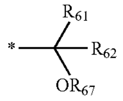

6-3

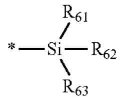

6-4

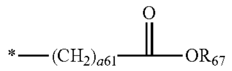

6-5

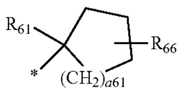

6-6

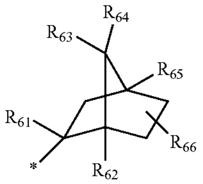

6-7

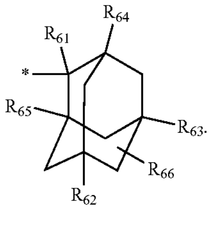

In Formulae 6-1 to 6-7, $a_{61}$ may be an integer from 0 to 6; $R_{61}$ to $R_{66}$ may each independently be at least one of hydrogen, a linear, branched, or cyclic $C_1$-$C_{20}$ monovalent hydrocarbon group that may include a heteroatom, and/or the like; $R_{67}$ may be a linear, branched, or cyclic $C_1$-$C_{20}$ monovalent hydrocarbon group that may include a heteroatom; and * indicates a binding site to a neighboring atom. In some example embodiments, two adjacent groups among $R_{61}$ to $R_{67}$ may be bonded to each other to form a ring.

In Formulae 6-4 and 6-5, $(CH_2)a_{61}$ may be a single bond when $a_{61}$ is 0.

The "monovalent hydrocarbon group" of $R_{61}$ to $R_{67}$ in Formulae 3-1 to 3-3 may be understood by referring to the case where $R_{21}$ in Formulae 2-1 and 2-2 is the "monovalent hydrocarbon group." In at least one embodiment, $X_51$ in Formula 5 may be hydrogen, a linear, branched, or cyclic $C_1$-$C_{20}$ monovalent hydrocarbon group that includes one or more polar moieties (e.g., selected from a hydroxyl group, a halogen, a cyano group, a carbonyl group, a carboxyl group, *—O—*', *—C(=O)O—*', —OC(=O)—*', *—S(=O)O—*', —OS(=O)—*', a lactone ring, a sultone ring, and a carboxylic anhydride moiety) and/or the like. Here, the "monovalent hydrocarbon group" in $X_{51}$ in Formula 5 may be understood by referring to the case where $R_{21}$ in Formulae 2-1 and 2-2 is the "monovalent hydrocarbon group", and essentially includes one or more polar moieties selected from a hydroxyl group, a halogen, a cyano group, a carbonyl group, a carboxyl group, *—O—*', *—C(=O)O—*', —OC(=O)—*', *—S(=O)O—*', —OS(=O)—*', a lactone ring, a sultone ring, and a carboxylic anhydride moiety.

In at least one embodiment, the repeating unit represented by Formula 4 may be represented by one of Formulae 4-1 and 4-2:

4-1

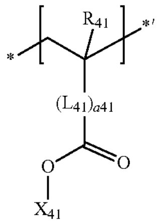

4-2

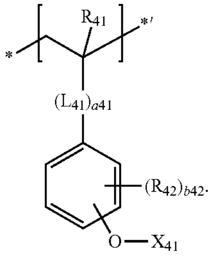

In Formulae 4-1 and 4-2, $L_{41}$ and $X_{41}$ may each be the same as defined in Formula 4; $a_{41}$ may be an integer from 1 to 4; $R_{42}$ may be hydrogen, a linear, branched, or cyclic $C_1$-$C_{20}$ monovalent hydrocarbon group that optionally includes a heteroatom; b42 may be an integer from 1 to 4; and * and *' each indicate a binding site to a neighboring atom. In at least some embodiment, $R_{42}$ may include a heteroatom.

The "monovalent hydrocarbon group" of $R_{42}$ in Formula 4-2 may be understood by referring to the case where $R_{21}$ in Formulae 2-1 and 2-2 is the "monovalent hydrocarbon group." In at least one embodiment, the repeating unit represented by Formula 5 may be represented by one of Formulae 5-1 and 5-2:

5-1

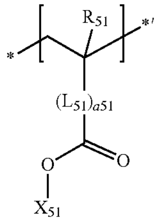

-continued 5-2

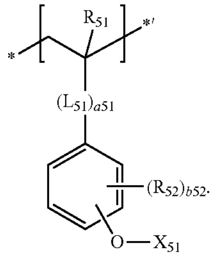

In Formulae 5-1 and 5-2, $L_{51}$ and $X_{51}$ may each be as defined in Formula 5; $a_{51}$ may be an integer from 1 to 4; $R_{52}$ may be hydrogen, a hydroxyl group, a linear, branched, or cyclic $C_1$-$C_{20}$ monovalent hydrocarbon group; b52 may be an integer from 1 to 4; and * and *' each indicate a binding site to a neighboring atom. In at least one embodiment, the $R_{52}$ may include a heteroatom.

The "monovalent hydrocarbon group" of $R_{52}$ in Formula 5-2 may be understood by referring to the case where $R_{21}$ in Formulae 2-1 and 2-2 is the "monovalent hydrocarbon group."

In at least one embodiment, the polymer may be a copolymer comprising the first repeating unit represented by Formula 1 and the second repeating unit represented by Formula 4. For example, the polymer may not include the repeating unit represented by Formula 5.

The polymer may have a weight average molecular weight (Mw) in a range of about 1,000 to 500,000, for example, about 3,000 to about 200,000, wherein the weight average molecular weight is measured by gel permeation chromatography using a tetrahydrofuran solvent and polystyrene as a standard material.

The polymer may have polydispersity index (PDI, Mw/Mn) in a range of about 1.0 to about 3.0, for example, about 1.0 to about 2.0. When PDI of the polymer is satisfied within the ranges above, the dispersibility and/or compatibility of the polymer may be easily adjusted. Accordingly, there is a less chance of remaining foreign substances on a pattern, and/or deterioration of a pattern profile may be reduced and/or minimized. Therefore, a photoresist composition including the polymer may become more suitable for forming a fine pattern.

The polymer may be prepared by any suitable method, For example, the polymer may be prepared by dissolving (or suspending) monomer(s) including unsaturated linkages in an organic solvent, followed by performing thermal polymerization. In at least one embodiment, the thermal polymerization may occur in the presence of a radical initiator.

When the polymer further includes the second repeating unit (e.g., selected from the repeating unit represented by Formula 4 and/or the repeating unit represented by Formula 5) a mole fraction (mol %) of each repeating unit derived from each monomer is as follows, but embodiments are not limited to:

i) the repeating unit represented by Formula 1 is included in an amount in a range of about 1 mol % to about 60 mol %, for example, about 5 mol % to about 50 mol %, and for example, about 10 mol % to about 50 mol %;

ii) the repeating unit represented by Formula 4 is included in an amount in a range of about 1 mol % to about 60 mol %, for example, about 5 mol % to about 50 mol %, and for example, about 10 mol % to about 50 mol %; and iii) the repeating unit represented by Formula 5 is included in an amount in a range of about 40 mol % to about 99 mol %, for example, about 50 mol % to about 95 mol %, and for example, about 50 mol % to about 90 mol %.

The structure (composition) of the polymer may be confirmed by performing FT-IR analysis, NMR analysis, X-ray fluorescence (XRF) analysis, mass spectrometry, UV analysis, single crystal X-ray structure analysis, powder X-ray diffraction (PXRD) analysis, liquid chromatography (LC) analysis, size exclusion chromatography (SEC) analysis, thermal analysis, and/or the like. A detailed example method for the confirmation is described in Examples below.

In general, when forming a pattern by using a photoresist composition, an acid generated from a photoacid generator by light exposure may diffuse in a photoresist film. Accordingly, the acid may penetrate even to an unexposed area so that the sensitivity and/or resolution of the photoresist composition may be lowered. That is, to improve the sensitivity and/or resolution of the photoresist composition, the diffusion of the acid may be effectively reduced, and a quencher may be used for this purpose.

However, the use of a quencher may not simply reduce the diffusion of the acid. To enhance the effect of the quencher while using the quencher in an appropriate amount, there is a need to improve the dispersion degree of the quencher and/or the compatibility of the quencher with a base resin.

In particular, to improve the compatibility of the quencher with a base resin, a method of coupling macromolecules has been studied, but such a method could not solve problems of a decrease in the solubility of the quencher in an organic solvent and/or a decrease in the compatibility of the quencher with a base resin. In addition, to improve the compatibility of the quencher with a base resin, a method of binding the quencher to a base resin itself has been studied, but practical applications had many difficulties due to problems of a decrease in the solubility of the base resin itself and/or the influence of the quencher on the contrast.

However, when the polymer according to at least one example embodiment is used as a quencher, the dispersibility of the quencher and/or the compatibility of the quencher with the base resin may be improved.

For example, when a low-molecular quencher is used, aggregation occurs in the base resin due to interactions among molecules of the low-molecular quencher (in particular, interactions by electrostatic attraction among ion-binding molecules).

Although a small amount of the quencher, without the polymer structure, may not be enough to effectively reduce the diffusion of the acid, use of the quencher having a polymer structure may improve the dispersibility of the acid in the base resin, and thus the diffusion of the acid may be effectively reduced even with a small amount of the quencher.

In addition, generally due to the difference in the diffusion distance of the acid, the roughness of the surface of the photoresist film may increase after development. In this regard, when a quencher having the polymer structure according to at least one embodiment is used, the diffusion of the acid may be effectively and evenly reduced, thereby improving the surface roughness.

Photoresist Composition

According to another aspect, a photoresist composition includes the polymer, an organic solvent, a base resin, and a photoacid generator. The photoresist composition may have properties including improved developability and/or improved resolution.

The solubility of the photoresist composition in a developing solution may be changed by exposure with high-energy rays. The photoresist composition may be, e.g., a positive photoresist composition that forms a positive photoresist pattern after an exposed area of a photoresist film is dissolved and removed; or a negative photoresist composition that forms a negative photoresist pattern after an unexposed area of a photoresist film is dissolved and removed. In addition, a sensitive photoresist composition according to at least one embodiment may be used in an alkali development process using an alkali developing solution for the development treatment when forming a photoresist pattern formation or may be used in a solvent development process using a developing solution containing an organic solvent (hereinafter also referred to as an organic developing solution) for the development treatment.

The polymer may be used in an amount in a range of about 0.1 parts by weight to about 40 parts by weight, for example, about 1 part by weight to about 20 parts by weight, based on 100 parts by weight of the base resin. In at least one embodiment, when the amount of the polymer is within these ranges, the polymer may exhibit quencher functions at an appropriate level, and formation of foreign particles may be reduced due to loss of any performance, e.g., a decrease in sensitivity, and/or a lack of solubility.

The polymer is the same as described above, and thus the organic solvent, the base resin, the photoacid generator, and additional components will be described below.

In addition, for use as the polymer including the repeating unit represented by Formula 1 in the photoresist composition, one type of the polymer or a combination of two or more different types of the polymer may be used.

<Organic Solvent>

The organic solvent included in the photoresist composition may include at least one organic solvent capable of dissolving and/or dispersing the polymer, the base resin, the photoacid generator, and optional components contained as necessary. One type of the organic solvent may be used, and/or a combination of two or more different types of the organic solvent may be used. Also, a mixed solvent in which water and an organic solvent are mixed may be used.

Examples of the organic solvent are an alcohol-based solvent, an ether-based solvent, a ketone-based solvent, an amide-based solvent, an ester-based solvent, a sulfoxide-based solvent, a hydrocarbon-based solvent, and/or the like.

In detail, examples of the alcohol-based solvent include a monoalcohol-based solvent, such as methanol, ethanol, n-propanol, isopropanol, 1-methoxy-2-propanol, 1-ethoxy-2-propanol, n-butanol, isobutanol, sec-butanol, tert-butanol, n-pentanol, isopentanol, 2-methylbutanol, sec-pentanol, tert-pentanol, 3-methoxybutanol, 3-methyl-3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol, diacetone alcohol, a polyhydric alcohol-based solvent (such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, and/or the like), a polyhydric alcohol-containing ether-based solvent (such as ethyleneglycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, diethylene glycol dimethyl ether, propylene glycol monomethyl ether, propylene glycol dimethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, and/or the like), and the like.

Examples of the ether-based solvent include a dialkyl ether-based solvent (such as diethyl ether, dipropyl ether, dibutyl ether, and/or the like); a cyclic ether-based solvent (such as tetrahydrofuran, tetrahydropyran, and/or the like); an aromatic ring-containing ether-based solvent (such as diphenyl ether, anisole, and/or the like); and the like.

Examples of the ketone-based solvent include a chain ketone-based solvent, such as acetone, methylethyl ketone, methyl-n-propyl ketone, methyl-n-butyl ketone, methyl-n-pentyl ketone, diethyl ketone, methyl isobutyl ketone, 2-heptanone, ethyl-n-butyl ketone, methyl-n-hexyl ketone, diisobutyl ketone, trimethylnonanone, a cyclic ketone solvent (such as cyclopentanone, cyclohexanone, cycloheptanone, cyclooctanone, methylcyclohexanone, and/or the like); 2,4-pentanedione; acetonylacetone; acetphenone; and/or the like.

Examples of the amide-based solvent include a cyclic amide-based solvent, such as N,N'-dimethylimidazolidinone, N-methyl-2-pyrrolidone, and the like; a chain amide-based solvent, such as N-methylformamide, N,N-dimethylformamide, N,N-diethylformamide, acetamide, N-methylacetamide, N,N-dimethylacetamide, N-methylpropionamide, and the like; and the like.

Examples of the ester-based solvent include an acetate ester-based solvent, such as methyl acetate, ethyl acetate, n-propyl acetate, isopropyl acetate, n-butyl acetate, isobutyl acetate, sec-butyl acetate, t-butyl acetate, n-pentyl acetate, isopentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, a polyhydric alcohol-containing ether carboxylate-based solvent (such as ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, and/or the like), a lactone-based solvent (such as y-butylolactone, 5-valerolactone, and the like; a carbonate-based solvent, such as dimethyl carbonate, diethyl carbonate, ethylene carbonate, propylene carbonate, and the like; a lactate ester-based solvent, such as methyl lactate, ethyl lactate, n-butyl lactate, n-amyl lactate, and/or the like); glycoldiacetate, methoxytriglycol acetate, propionic acid ethyl, propionic acid n-butyl, propionic acid isoamyl, diethyloxalate, di-n-butyloxalate, methyl acetoacetate, ethyl acetoacetate, malonic acid diethyl, phthalic acid dimethyl, phthalic diethyl, and/or the like.

Examples of the sulfoxide-based solvent include dimethyl sulfoxide, diethyl sulfoxide, and/or the like.

Examples of the hydrocarbon-based solvent include an aliphatic hydrocarbon-based solvent (such as n-pentane, isopentane, n-hexane, isohexane, n-heptane, isoheptane, 2,2,4-trimethyl pentane, n-octane, isooctane, cyclohexane, methylcyclohexane, and/or the like), an aromatic hydrocarbon-based solvent (such as benzene, toluene, xylene, mesitylene, ethyl benzene, trimethyl benzene, methylethyl benzene, n-propyl benzene, isopropyl benzene, diethyl benzene, isobutyl benzene, triethyl benzene, diisopropyl benzene, n-amylnaphthalene, and/or the like), and/or the like.

In at least one embodiment, the organic solvent may be selected from an alcohol-based solvent, an amide-based solvent, an ester-based solvent, a sulfoxide-based solvent, and any combination thereof. For example, in one or more embodiments, the organic solvent may be selected from propylene glycol monomethyl ether, propylene glycol monoethyl ether, propylene glycol monomethyl ether acetate, N-methyl-2-pyrrolidone, N,N-dimethylacetamide, ethyl lactate, dimethyl sulfoxide, and any combination thereof.

In at least one embodiment, when an acetal-type acid labile group is used, the organic solvent may further include alcohol having a high boiling point, such as diethylene glycol, propylene glycol, glycerol, 1,4-butanediol, 1,3-butanediol, and/or the like, to accelerate a deprotection reaction of acetal.

The organic solvent may be used in an amount in a range of about 200 parts by weight to about 5,000 parts by weight, for example, about 400 parts by weight to about 3,000 parts by weight, based on 100 parts by weight of the base resin.

<Base Resin>

The base resin may include a repeating unit represented by Formula 4 and including an acid labile group:

Formula 4

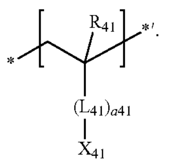

In Formula 4, $R_{41}$, $L_{41}$, a41, and $X_{41}$ may each be the same as described herein.

The base resin including the repeating unit represented by Formula 4 may be decomposed under the action of an acid to generate a carboxyl group, and thus may be converted to have alkali solubility.

In at least one embodiment, the base resin may further include, in addition to the repeating unit represented by Formula 4, a repeating unit represented by Formula 5:

Formula 5

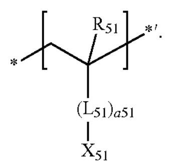

In Formula 5, $R_{51}$, $L_{51}$, a51, and $X_{51}$ may each be the same as described herein.

For example, in an ArF lithography process, $X_{51}$ may include a lactone ring as a polar moiety, and in KrF, EB, and EUV lithography processes, $X_{51}$ may be phenol.

In at least one embodiment, the base resin may not include a moiety including an anion and/or a cation.

The base resin may have a weight average molecular weight (Mw) in a range of about 1,000 to 500,000, for example, about 3,000 to about 100,000, wherein the weight average molecular weight (Mw) is measured by gel permeation chromatography using a tetrahydrofuran solvent and polystyrene as a standard material.

The base resin may have PDI (Mw/Mn) in a range of about 1.0 to about 3.0, for example, about 1.0 to about 2.0. When the PDI of the base resin is satisfied within the ranges above, there is a less chance of remaining foreign substances on a pattern, or deterioration of a pattern profile may be minimized. Accordingly, the photoresist composition may be more suitable for forming a fine pattern.

The base resin may be prepared by any suitable method. For example, the base resin may be prepared by dissolving monomer(s) including unsaturated linkages in an organic solvent, followed by performing thermal polymerization in the presence of a radical initiator.

In the base resin, a mole fraction (mol %) of each repeating unit derived from each monomer is as follows, but is not limited thereto:

i) the repeating unit represented by Formula 4 is included in an amount in a range of about 1 mol % to about 60 mol %, for example, about 5 mol % to about 50 mol %, and for example, about 10 mol % to about 50 mol %; and ii) the repeating unit represented by Formula 5 is included in an amount in a range of about 40 mol % to about 99 mol %, for example, about 50 mol % to about 95 mol %, and for example, about 50 mol % to about 90 mol %.

The base resin may be a homopolymer and/or may include a mixture of two or more types of polymers having a different composition, weight average molecular weight (Mw), and/or PDI (Mw/Mn).

Photoacid Generator

The photoacid generator may include any compound configured to generate an acid upon exposure to high-energy rays, such as UV, DUV, EB, EUV, X-ray, excimer laser, γ-ray, and/or the like.

The photoacid generator may include, e.g., a sulfonium salt, an iodonium salt, a combination thereof, and/or the like.

In at least one embodiment, the photoacid generator may be represented by Formula 7:

$A_{71}^{+}B_{71}^{-}$ Formula7 wherein, in Formula 7, $A_{71}^{+}$may be represented by Formula 7A, and $B_{71}^{-}$may be represented by one of Formulae 7B to 7D, and $A_{71}^{+}$ and $B_{71}^{-}$ may be linked via, e.g., an ionic bond and/or a carbon-carbon covalent bond:

7A

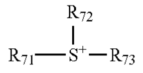

7B

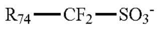

7C

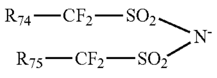

-continued

7D

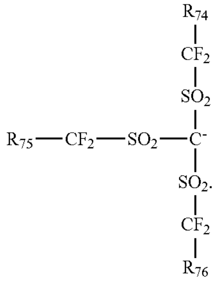

In Formulae 7A to 7D, $R_{71}$ to $R_{73}$ may each independently be a linear, branched, or cyclic $C_1$-$C_{20}$ monovalent hydrocarbon group, and $R_{74}$ to $R_{76}$ may each independently be F; or a linear, branched, or cyclic $C_1$-$C_{20}$ monovalent hydrocarbon group. In at least one embodiment, the $C_1$-$C_{20}$ monovalent hydrocarbon group may include a heteroatom. In at least one embodiment, two adjacent groups among $R_{71}$ to $R_{73}$ may be bonded to each other to form a ring.

In Formula 7A, $R_{71}$ to $R_{73}$ may each be the same as described in connection with $R_{31}$ to $R_{35}$ in Formula 3-1.

Regarding $R_{74}$ to $R_{76}$ in Formulae 7B to 7D, examples of the monovalent hydrocarbon include a linear or branched alkyl group (e.g., a methyl group, an ethyl group, a propyl group, an isopropyl group, a butyl group, an isobutyl group, a sec-butyl group, a tert-butyl group, a pentyl group, a neopentyl group, a hexyl group, a heptyl group, a 2-ethylhexyl group, a nonyl group, an undecyl group, a tridecyl group, a pentadecyl group, a heptadecyl group, and an eicosanyl group); a monovalent saturated alicyclic hydrocarbon group (e.g., a cyclopentyl group, a cyclohexyl group, a 1-adamantyl group, a 2-adamantyl group, a 1-adamantylmethyl group, a norbornyl group, a norbornylmethyl group, a tricyclotricyclodecanyl group, a tetracyclododecanyl group, a tetracyclododecanylmethyl group, and a dicyclohexylmethyl group); a monovalent unsaturated aliphatic hydrocarbon group (e.g., an aryl group and a 3-cyclohexenyl group); an aryl group (e.g., a phenyl group, a 1-naphthyl group, and a 2-naphthyl group); an arylalkyl group (e.g., a benzyl group and a diphenylmethyl group); a heteroatom-containing monovalent hydrocarbon group (e.g., a tetrahydrofuranyl group, a methoxymethyl group, an ethoxymethyl group, a methylthiomethyl group, an acetamidemethyl group, a trifluoroethyl group, a (2-methoxyethoxy)methyl group, an acetoxymethyl group, a 2-carboxy-1-cyclohexyl group, a 2-oxopropyl group, a 4-oxo-1-adamantyl group, and a 3-oxocyclohexyl group); and/or the like. In addition, among these groups, some hydrogen atoms may be substituted with a moiety including a heteroatom (such as oxygen, sulfur, nitrogen, a halogen atom, and/or the like), or some carbon atoms may be replaced by a moiety including a heteroatom, such as oxygen, sulfur, nitrogen, and/or the like.

Accordingly, these groups may each include a hydroxy group, a cyano group, a carbonyl group, a carboxyl group, an ether linkage, an ester linkage, a sulfonic ester linkage, a carbonate, a lactone ring, a sultone ring, a carboxylic anhydride moiety, a haloalkyl moiety, and/or the like.

For example, in Formula 7, $A_{71}^{+}$may be represented by Formula 7A, and $B_{71}^{-}$may be represented by Formula 7B. For example, $R_{71}$ to $R_{73}$ in Formula 7A may each be a phenyl group, and $R_{74}$ in Formula 7B may be a propyl group substituted with F.

The photoacid generator may be included in an amount in a range of about 0 parts by weight to about 40 parts by weight, about 0.1 parts by weight to about 40 parts by weight, or about 0.1 parts by weight to about 20 parts by weight, based on 100 parts by weight of the base resin. When the amount of the photoacid generator is satisfied within the ranges above, proper resolution may be achieved, and problems related to foreign particles after development or during stripping may be reduced.

In at least one example, one type of the photoacid generator may be used, and/or a combination of two or more different types of the photoacid generator may be used.

Additional Components

In at least some embodiment, the photoresist composition may further include a surfactant, a cross-linking agent, a leveling agent, a colorant, and/or a combination thereof, as needed.

For example, the photoresist composition may further include a surfactant to improve coating properties, developability, and/or the like. Examples of the surfactant may include a non-ionic surfactant (such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, polyethylene glycol distearate, and/or the like) and/or the like. For use as the surfactant, a commercially available product may be used, and/or a synthetic product may be used. Examples of the commercially available product are KP341 (manufactured by Shin-Etsu Chemical Co., Ltd.), POLYFLOW No. 75 and POLYFLOW No. 95 (manufactured by Kyoeisha Chemical Co., Ltd.), FTOP EF301, FTOP EF303, and FTOP EF352 (manufactured by Mitsubishi Materials Electronic Chemicals Co., Ltd.), MEGAFACE F171 (registered trademark), MEGAFACE F173, $R_{40}$, $R_{41}$, and $R_{43}$ (manufactured by DIC Corporation), Fluorad FC430 (registered trademark) and Fluorad FC431 (manufactured by 3M Company), AsahiGuard AG710 (product of AGC Corporation), Surflon S-382 (registered trademark), Surflon SC-101, Surflon SC-102, Surflon SC-103, Surflon SC-104, Surflon SC-105, and Surflon SC-106 (manufactured by AGC Seimi Chemical Co., Ltd.), and/or the like.

The surfactant may be included in an amount in a range of about 0 parts by weight to about 20 parts by weight based on 100 parts by weight of the base resin. In at least one embodiment, one type of the surfactant may be used, and/or a combination of two or more different types of the surfactant may be used.

A method of preparing the photoresist composition is not particularly limited. For example, a method of mixing the polymer, the base resin, the photoacid generator, and optional components added as necessary in the organic solvent may be used.

The temperature or time at the mixing is not particularly limited. Filtration may be performed after the mixing as needed.

Pattern forming method

Figure 2:
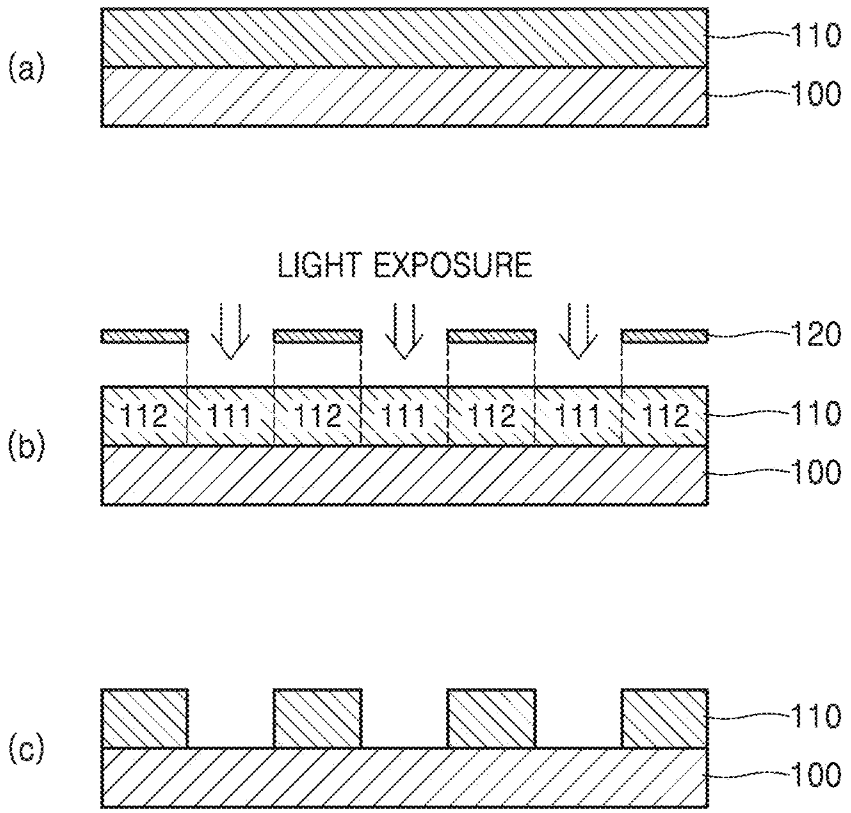
FIG. 2 is a side cross-sectional view illustrating a pattern forming method according to an embodiment.

Hereinafter, a method of forming a pattern according to at least one embodiment will be described in detail with reference to FIGS. 1 and 2. FIG. 1 is a flowchart representing a pattern forming method according to the at least one embodiment, and FIG. 2 is a side cross-sectional view illustrating a pattern forming method according to the at least one embodiment. Hereinafter, a method of forming a pattern by using a positive photoresist composition will be described in detail as an example, but embodiments are not limited thereto. For example, the method may use a negative photoresist composition, and the description adapted accordingly.

Referring to FIG. 1, a method of forming a pattern includes: forming a photoresist film by applying a photoresist composition (S101); exposing at least a portion of the photoresist film with high-energy rays (S102); and developing the exposed photoresist film by using a developing solution (S103). In some examples, the steps above may be omitted as necessary or may be performed in different orders.

First, a board 100 is prepared. The board 100 may be, for example, a semiconductor board, such as a silicon board or a germanium board, and/or may be formed of glass, quartz, ceramic, copper, and/or the like. In at least one embodiment, the board 100 may include a Group III-V compound, such as GaP, GaAs, GaSb, and/or the like.

A photoresist film 110 may be formed by coating the board 100 with a photoresist composition to a desired thickness according to a coating method. In at least one embodiment, a heating process may be performed thereon to remove an organic solvent remaining in the photoresist film 110. The coating method may include, e.g., spin coating, dipping, roller coating, and/or the like. Among these methods, spin coating may be particularly used, and the photoresist film 110 having a desired thickness may be formed by adjusting the viscosity, concentration, and/or spin speed of the photoresist composition. In at least one embodiment, a thickness of the photoresist film 110 may be in a range of about 10 nm to about 300 nm. In one or more embodiments, a thickness of the photoresist film 110 may be in a range of about 30 nm to about 200 nm.

In at least one embodiment, the lower limit of a pre-baking temperature may be about 60° C. or higher, for example, about 80° C. or higher. In addition, the upper limit of a pre-baking temperature may be about 150° C. or lower, for example, about 140° C. or lower. The lower limit of a pre-baking time may be about 5 seconds or more, for example, about 10 seconds or more. The upper limit of a pre-baking time may be about 600 seconds or less, for example, about 300 seconds or less. Before coating the board 100 with the photoresist composition, a film to be etched (not shown) may be further formed on the board 100. The film to be etched may refer to a layer in which an image is transferred from a photoresist pattern and converted into a predetermined pattern. In an embodiment, the film to be etched may be formed to include, for example, an insulating material, such as silicon oxide, silicon nitride, silicon oxynitride, and/or the like. In one or more embodiments, the film to be etched may be formed to include a conductive material, such as metal, metal nitride, metal silicide, or metal silicide nitride. In one or more embodiments, the film to be etched may be formed to include a semiconductor material, such as polysilicon.

In at least one embodiment, an antireflection layer may be further formed on the board 100 to exhibit efficiency of the photoresist at most. The antireflection layer may be an organic-based antireflection layer or an inorganic-based antireflection layer.

In at least one embodiment, a protective layer may be further provided on the photoresist film 110 to reduce the influence of alkaline impurities included in the process. In addition, when performing immersion exposure, for example, a protective film against immersion may be provided on the photoresist film 110 to avoid direct contact between an immersion medium and the photoresist film 110.

Next, at least a portion of the photoresist film 110 may be exposed with high-energy rays. For example, high-energy rays passing through a mask 120 may be irradiated to a portion of the photoresist film 110. Accordingly, the photoresist film 110 may have an exposed area 111 and an unexposed area 112.

For example, the exposure may be carried out by irradiating high-energy rays through a mask having a predetermined pattern and by using liquid (such as water or the like), as a medium in some cases. Examples of the high-energy rays are electromagnetic waves, such as ultraviolet rays, far-ultraviolet rays, extreme ultraviolet rays (EUV rays, wavelength of 13.5 nm), X-rays, γ-rays, charged particle beams (such as electron beams (EBs), a rays, and/or the like); and/or the like. The irradiation of such high-energy rays may be collectively referred to as "exposure". In at least one embodiment, the medium may serve as a transfer medium and/or a heat sink.

For use as a light source of the exposure, various types of irradiation including irradiating laser beams in the ultraviolet region, such as KrF excimer laser (wavelength of 248 nm), ArF excimer laser (wavelength of 193 nm), and an F2 excimer laser (wavelength of 157 nm), irradiating harmonic laser beams in the far ultraviolet or vacuum ultraviolet region by a wavelength conversion method using laser beams from a solid-state laser source (e.g., YAG or semiconductor laser), irradiating electron beams or EUV rays, and/or the like. Upon the exposure, the exposure may be performed through a mask corresponding to a desired pattern.

However, when the light source of the exposure is electron beams, the exposure may be performed by direct drawing without using a mask.

The integral dose of the high-energy rays may be less than or equal to about 2,000 $mJ/cm^2$, for example, less than or equal to about 500 $mJ/cm^2$, in the case of using EUV rays as the high-energy rays. In addition, in the case of using electron beams as the high-energy rays, the integral dose of the high-energy rays may be less than or equal to about 5,000 $pC/cm^2$, for example, less than or equal to about 1,000 $pC/cm^2$.

In addition, post-exposure baking (PEB) may be performed after the exposure. The lower limit of a PEB temperature may be about 50° C. or higher, for example, about 80° C. or higher. The upper limit of a PEB temperature may be about 180° C. or less, for example, about 130° C. or less. The lower limit of a PEB time may be about 5 seconds or more, for example, about 10 seconds or more. The upper limit of a PEB time may be about 600 seconds or less, for example, about 300 seconds or less.

Next, the exposed photoresist film 110 may be developed by using a developing solution. The exposed area 111 may be washed away by the developing solution, whereas the unexposed area 112 may remain without being washed away by the developing solution.

For use as the developing solution, an alkali developing solution, a developing solution containing an organic solvent (hereinafter also referred to as "organic developing solution"), and/or the like may be used. As a developing method, a dipping method, a puddle method, a spray method, a dynamic administration method, and/or the like may be used. In at least one embodiment, the developing temperature may be, for example, about 5° C. or more and about 60° C. or less, and the developing time may be, for example, about 5 seconds or more and about 300 seconds or less.

The alkali developing solution may be, for example, an alkaline aqueous solution which dissolves at least one alkaline compound. For example, the alkali developing solution may include at least one of sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethyl ammonium hydroxide (TMAH), pyrrole, piperidine, choline, 1,8-diazabicyclo[5.4.0]-7-undecene (DBU), 1,5-diazabicyclo[4.3.0]-5-nonene, and/or the like. The alkaline developing solution may further include a surfactant.

The lower limit of the amount of the alkaline compound in the alkaline developing solution may be about 0.1 mass % or more, for example, about 0.5 mass % or more, and for example, about 1 mass % or more. In addition, the upper limit of the amount of the alkaline compound in the alkaline developing solution may be about 20 mass % or less, for example, about 10 mass % or less, and for example, about 5 mass % or less.

After the development, a resulting photoresist pattern may be washed with ultrapure water, and subsequently, the water remaining on the board 100 and the pattern may be removed.

As an organic solvent contained in the organic developing solution, for example, the same organic solvent as the organic solvent described in the <Organic solvent>of the [Resist composition] may be used.

The lower limit of the amount of the organic solvent in the organic developing solution may be about 80 mass % or more, for example, about 90 mass % or more, and for example, about 95 mass % or more, and for example, about 99 mass % or more.

The organic developing solution may also include a surfactant. In addition, the organic developing solution may include a trace amount of moisture. In addition, upon the development, the solvent may be substituted with a solvent of a different kind from the organic developing solution to stop the development.

The photoresist pattern resulting from the development may be further washed. As a washing solution, ultrapure water, a liquid rinse, and/or the like may be used. The liquid rinse is not particularly limited as long as it does not dissolve the photoresist pattern. For example, a solution containing a general organic solvent may be used.

For example, the liquid rinse may be an alcohol-based solvent or an ester-based solvent. After the washing, the liquid rinse remaining on the board and the pattern may be removed. In addition, when ultrapure water is used, the water remaining on the board and the pattern may be removed.

In addition, the developing solution may be used either individually or in a combination of two or more.

After the photoresist pattern is formed as described above, an etching process may be performed thereon to obtain a patterned wiring board. The etching method may be performed by known methods including dry etching using plasma gas; wet etching using an alkali solution, a cupric chloride solution, a ferric chloride solution; and/or the like.

After forming the resist pattern, plating may be performed. Although not particularly limited, the plating method may include, for example, copper plating, solder plating, nickel plating, gold plating, and/or the like.

The photoresist pattern remaining after the etching may be exfoliated with an organic solvent. Although not particularly limited, examples of the organic solvent are propylene glycol monomethyl ether acetate (PGMEA) propylene glycol monomethyl ether (PGME), ethyl lactate (EL), and/or the like. Although not particularly limited, examples of the exfoliation method are an immersion method, a spray method, and the like. In addition, the wiring board on which the photoresist pattern is formed may be a multilayer wiring board and may have through holes with a small diameter.

In at least one embodiment, after the formation of the photoresist pattern, the wiring board may be formed by a so-called lift-off process in which metal is deposited in a vacuum and then the photoresist pattern is dissolved in a solution.

The disclosure will be described in more detail with reference to Examples and Comparative Examples below, but the technical scope of the disclosure is not limited only thereto.

EXAMPLES

Synthesis Example 1: Synthesis of PDQ1 (BITPS-TSA/ECP)

(1) Synthesis of TSA-MA

Trifluoro(hydroxyethyl)methane sulfonamide (TSA) (5 g, 0.025 mol) and methane

Figure 3:
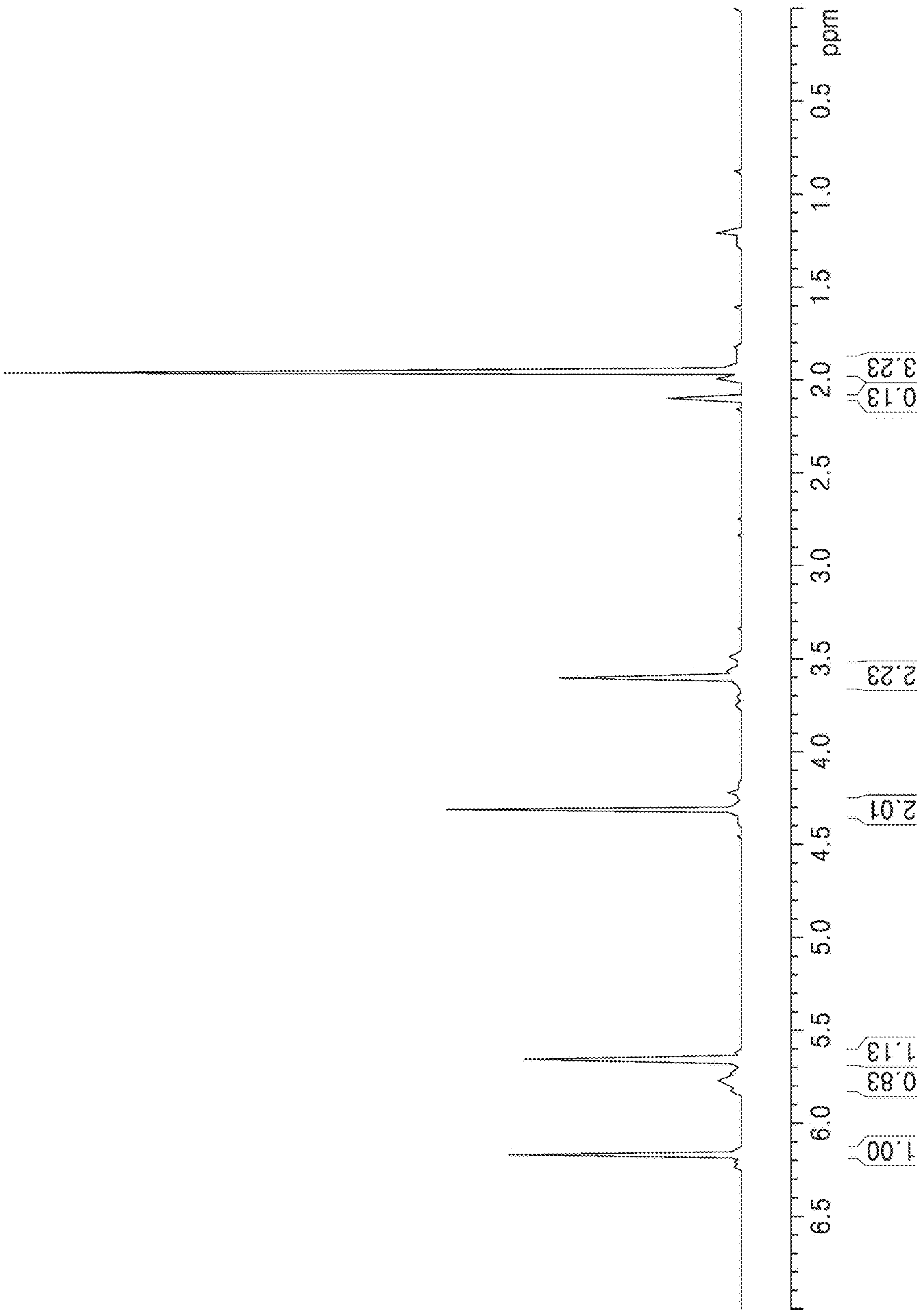
FIG. 3 is a diagram showing a $^1$H-NMR spectrum.

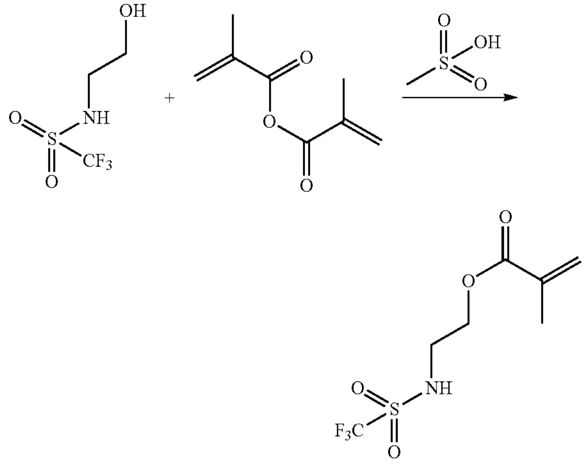

sulfonic acid (1 g, 0.0025 mol) were added to a round-bottom flask, and methacryl anhydride (MA) (3.99 g, 0.025 mol) was slowly added thereto. Then, the reaction was allowed to proceed at room temperature for 4 hours. After completion of the reaction, the reaction mixture was dissolved in 50 mL of ether, and 50 mL of 1 N NaOH was added thereto, followed by stirring for 30 minutes. After removing the water layer, 50 mL of 5% sodium bicarbonate aqueous solution was added thereto, and the resultant solution was stirred again for 20 minutes. After removing the water layer, a washing process was performed thereon three times with distilled water. After the resultant solution was dissolved in a small amount of ether and allowed for precipitation by using n-hexane, the solid product thus obtained was dried at room temperature for 24 hours to obtain 6 g of TSA-MA. The results of $^1$H-NMR analysis on the TSA-MA are shown in FIG. 3.

(2) Synthesis of BITPS-TSA/ECP

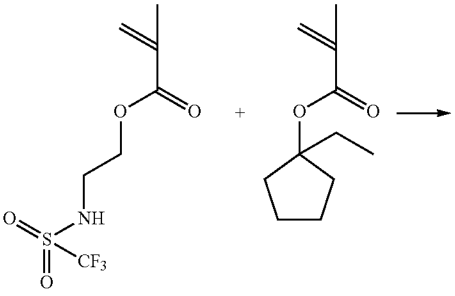

TSA-MA ECP-MA

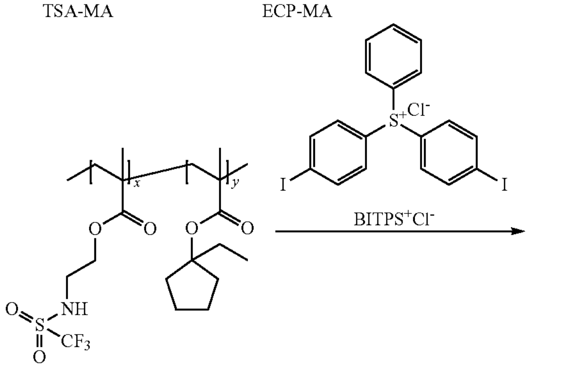

TSA/ECP

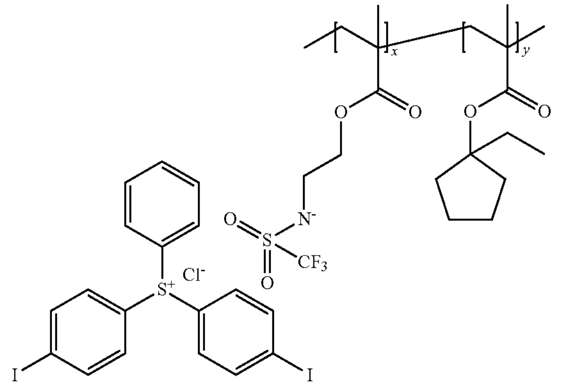

BITPS-TSA/ECP

TSA-MA (1 g, 3.8 mmol), ECP-MA (ethylene-cyclopentane-MA) (2.1 g, 11.2 mmol), and V601 (0.7 g, 3.1 mmol) were added to a vial and dissolved in 15 mL of dioxane.

The reaction was allowed to proceed at 70° C. for 4 hours and to precipitate by using n-hexane to synthesize TSA/ECP (x:y=1:2, Mw=10,500, and PDI=1.8).

Next, the TSA/ECP (0.2 g) thus obtained and bi-iodized triphenyl sulfonium (BITPS)+CI- (0.27 g) were added to a vial, and 10 mL of dichloromethane was added thereto to dissolve the reactants. Then, 10 mL of 1 N NaOH was added thereto, and the resultant solution was stirred for 4 hours. After removing the solvent therefrom by distillation under reduced pressure, the resultant product was dissolved in a small amount of THF and then precipitated by using distilled water. The powder thus obtained was dissolved again in dichloromethane, and the moisture was removed therefrom by using sodium sulfate. After removing the solvent therefrom again by distillation under reduced pressure, BITPS-TSA/ECP was obtained through an ion exchange reaction.

Figure 4:
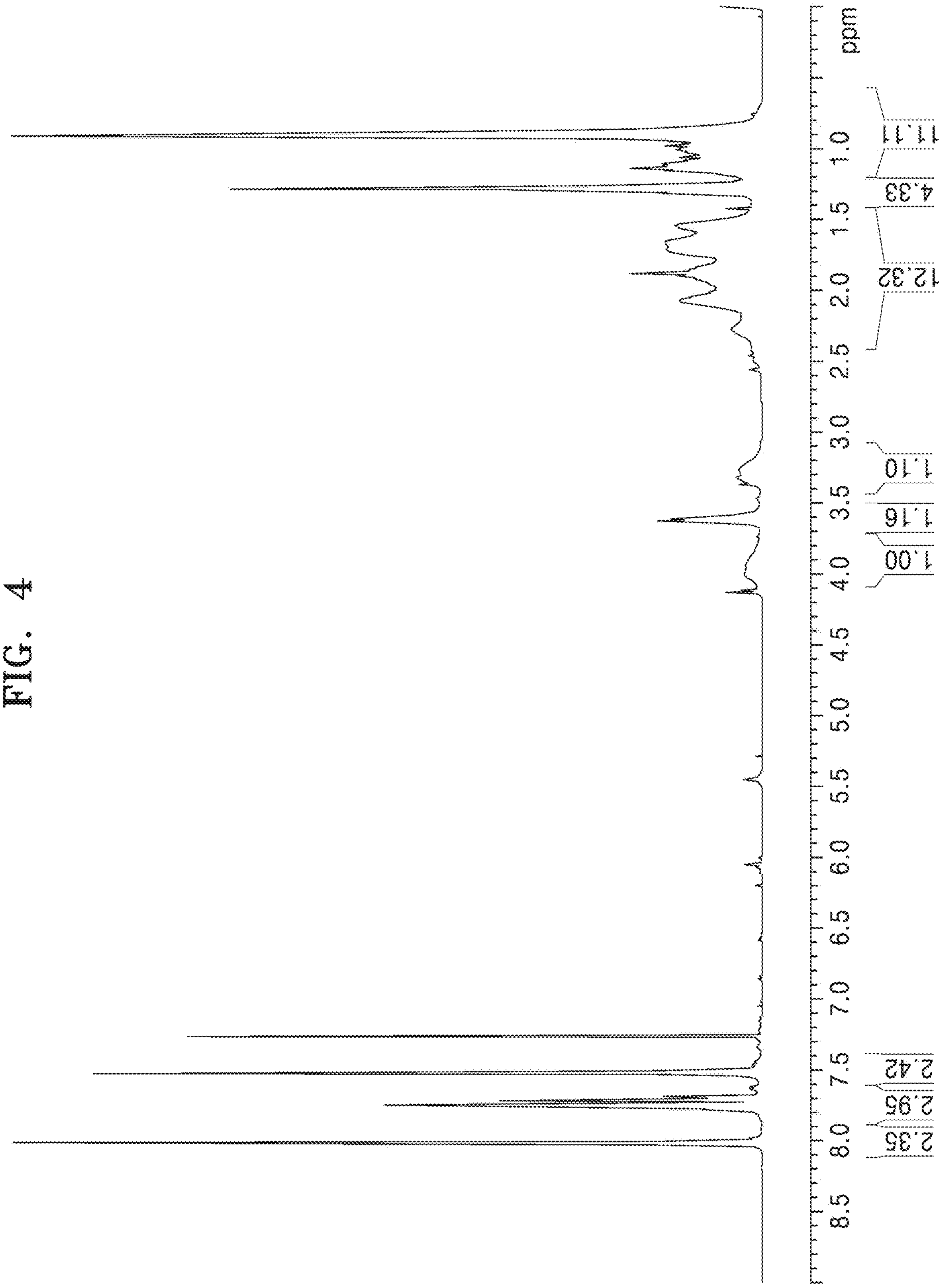
FIG. 4 is a diagram showing a $^1$H-NMR spectrum.

The BITPS-TSA/ECP thus obtained was confirmed by $^1$H-NMR, and the results thereof are shown in FIG. 4.

Synthesis Example A: Synthesis of Base Resin 1 (HS/ECP)

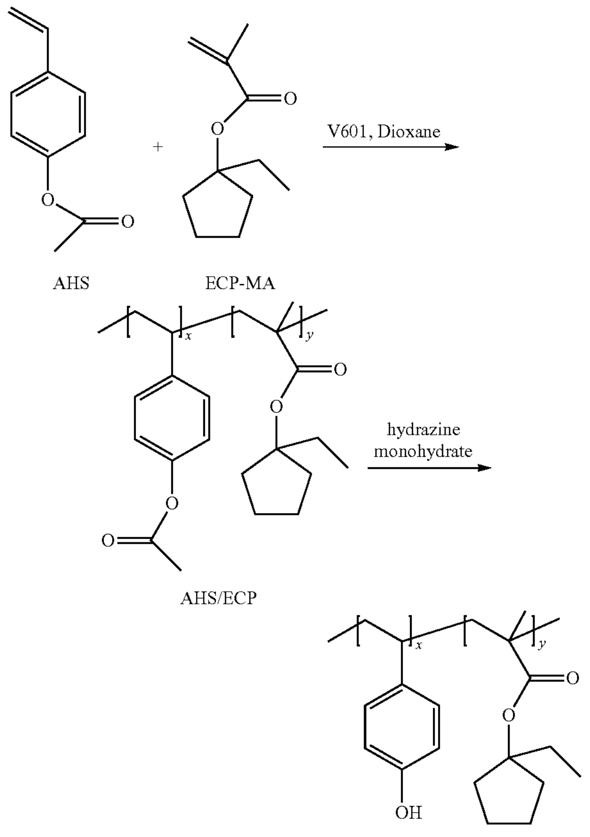

AHS
ECP-MA
AHS/ECP
HS/ECP

Figure 5:
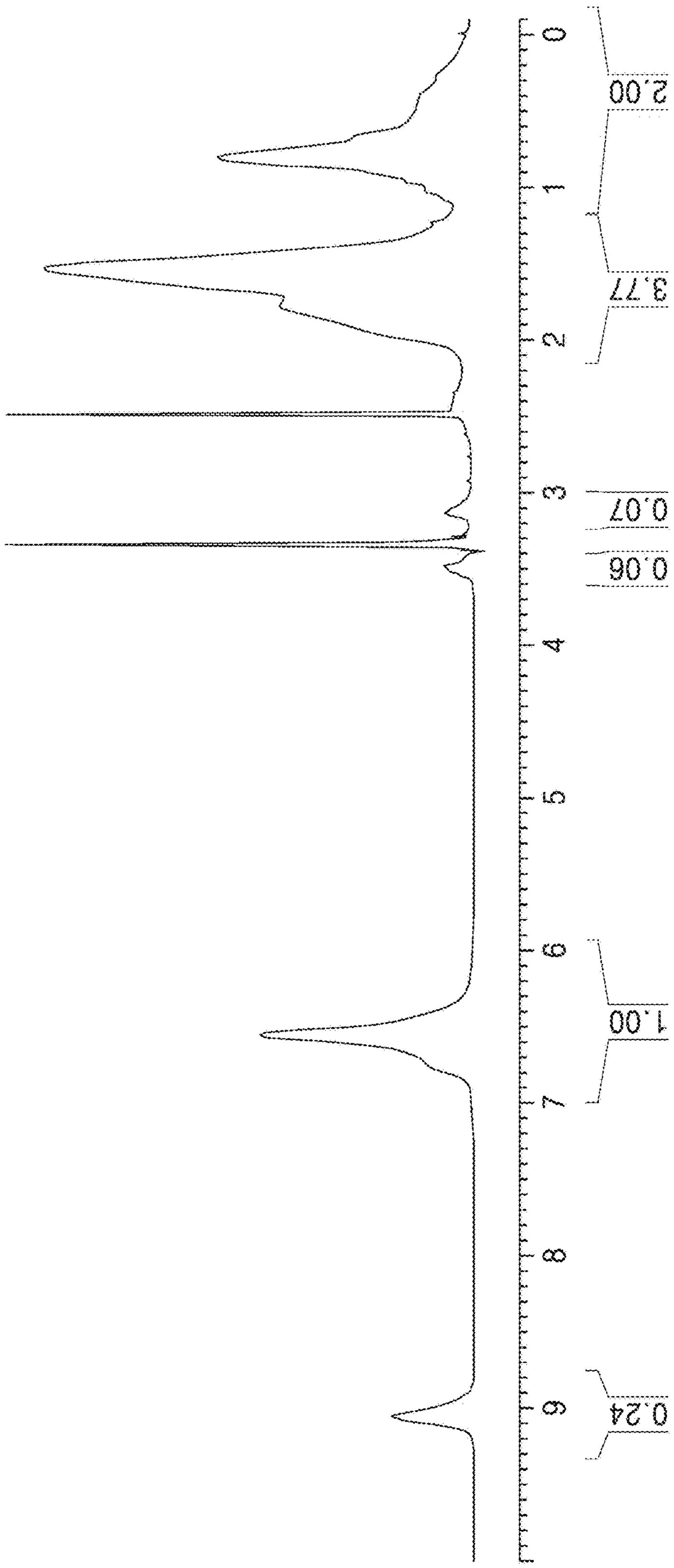
FIG. 5 is a diagram showing a 1H-NMR spectrum.

Acetoxystyrene (AHS) (3 g, 18.5 mmol), ethylcyclopentyl methacrylate (ECP-MA) (3.4 g, 18.5 mmol), and V601 (0.9 g, 3.7 mmol) were dissolved in 30 mL of dioxane, and a reaction was allowed to proceed at 80° C. for 4 hours. Here, hydrazine monohydrate (3 g) was added thereto, and the reaction was further allowed to proceed at room temperature for 2 hours. After completion of the reaction, 50 mL of distilled water and 5 g of acetic acid were added thereto, and an extraction process was performed thereon by using ethyl acetate. An organic layer thus obtained was collected and distilled under reduced pressure, and then allowed for precipitation by using n-hexane. The solid product thus obtained was dried at 40° C. for 24 hours to synthesize hydroxy styrene (HS)/ECP (x:y=5:5, Mw=5,000, and PDI=1.3). The results of $^1$H-NMR analysis on the HS/ECP are shown in FIG. 5.

Preparation Example 1: Preparation of Quencher Solution 1

The polymer obtained in Synthesis Example 1 was dissolved in a propylene glycol methyl ether/propylene glycol methyl ether acetate (PGME/PGMEA) 7/3 (wt/wt) solution at 1.6 wt % to prepare 0.032 mmol of Quencher Solution 1.

Comparative Preparation Example 1: Preparation of quencher-free solution

The base resin (HS/ECP) obtained in Synthesis Example A was dissolved in a PGME/PGMEA 7/3 (wt/wt) solution at 1.6 wt % to prepare a quencher-free solution.

Comparative Preparation Example 2: Preparation of Low Molecular Weight Quencher Solution The base resin (HS/ECP) obtained in Synthesis Example A was dissolved in a PGME/PGMEA 7/3 (wt/wt) solution at 1.6 wt %, and 0.032 mmol of Compound BITPS-TSA-Ad as a low molecular weight quencher was added thereto to prepare a low molecular weight quencher solution.

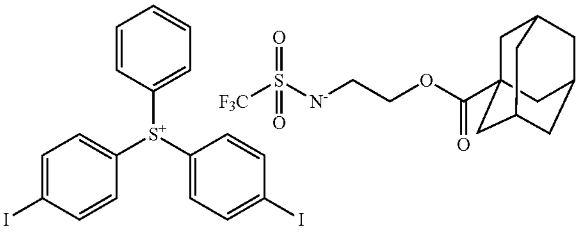 [SMILES: Ic1ccc([S+](c2ccccc2)c2ccc(I)cc2)cc1 ; O=C(OCC[N-]S(=O)(=O)C(F)(F)F)C12CC3CC(CC(C3)C1)C2]

BITPS-TSA-Ad

Preparation Example A: Preparation of photoacid generator solution

The base resin (HS/ECP) obtained in Synthesis Example A was dissolved in a PGME/PGMEA 7/3 (wt/wt) solution at 1.6 wt %, and 0.048 mmol of TPS/perfluorobutanesulfonic acid (PFBS) as a photoacid generator was added thereto to prepare a photoacid generator solution.

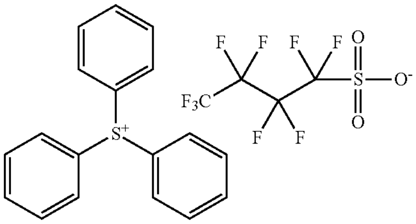 [SMILES: c1ccc([S+](c2ccccc2)c2ccccc2)cc1 ; O=S(=O)([O-])C(F)(F)C(F)(F)C(F)(F)C(F)(F)F]

TPS/PFBS

Evaluation Example 1: Evaluation of Acid Diffusion Length (ADL) and Surface Roughness (Ra)

(ADL evaluation)

The ADL evaluation was performed by using the method disclosed in Macromolecules (43(9)4275 (published in 2010). In detail, the method is as follows.

First, a 12-inch round silicon wafer board was pre-treated for 10 minutes under a UV Ozone (UVO) cleaning system. The silicon wafer board was spin-coated with the quencher solution of Preparation Example 1 at a speed of 1,500 rpm for 30 seconds to form a first film having a thickness of 100 nm.

Polydimethylsiloxane (PDMS) that was subjected to hydrophilization treatment by UVO cleaner equipment was spin-coated with the photoacid generator solution of Preparation Example A at a speed of 1,500 rpm for 30 seconds, and then, exposed to deep UV (DUV) rays having a wavelength of 248 nm at 250 $mJ/cm^2$ to form a second film. Due to the light exposure, an acid was generated from the photoacid generator in the second film.

Next, the second film overlapped with the first film so that the films were brought into contact with each other, and a pressure was applied thereto. Accordingly, the PDMS was removed while transferring the second film to the first film, thereby obtaining a laminate consisting of the silicon wafer board, the first film, and the second film. The laminate was maintained at 90° C. for 60 seconds to allow diffusion of the acid generated in the second film into the first film. Then, the laminate was washed with a tetramethyl ammonium hydroxide (TMAH) aqueous solution (2.38 wt %), and a thickness of the first film remained after the washing was measured to evaluate ADL.

The ADL for each sample was evaluated under the same conditions, except that, in forming the first film, each of the quencher-free solution of Comparative Preparation Example 1 and the solution of Comparative Preparation Example 2 was used instead of the quencher solution of Preparation Example 1, and the results thereof are shown in Table 1.

TABLE 1

| First film | Preparation Example 1 | Comparative Preparation Example 1 | Comparative Preparation Example 2 |
|---|---|---|---|
| ADL (nm) | 5.2 | 12.7 | 3 |

(Rq Evaluation)

Among the samples evaluated for the ADL, the surface of the first film newly exposed by the TMAH phenomenon was observed through an atomic force microscope, and Rq was calculated from the average value of the observed heights, and the Rq evaluation results are shown in Table 2.

TABLE 2

| First film | Preparation Example 1 | Comparative Preparation Example 1 | Comparative Preparation Example 2 |
|---|---|---|---|
| Rq (nm) | 0.592 | 0.987 | 0.897 |

Referring to Tables 1 and 2, it was confirmed that the ADL value of the first film of Preparation Example 1 was similar to (e.g., with an order of magnitude) that of Comparative Preparation Example 2, and that the Rq value of the first film of Preparation Example 1 was significantly reduced. Accordingly, it can be inferred that, when the acid generated by the exposure was diffused, the quencher in Preparation Example 1 was diffused more evenly than in Comparative Preparation Example 2, so that the diffusion of the acid was prevented more evenly.

As described above, according to the one or more embodiments, a quencher having improved dispersibility and/or improved compatibility with a base resin and a photoresist composition including the quencher may be provided.

It should be understood that the example embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A polymer comprising a first repeating unit represented by Formula 1:

[Formula 1]

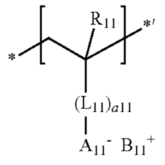

wherein, in Formula 1, $R_{11}$ is at least one of hydrogen, a halogen, $CH_3$, $CH_2F$, $CHF_2$, or CF3, $L_{11}$ is at least one of a single bond, a substituted or unsubstituted $C_1$-$C_1$ alkylene group, a substituted or unsubstituted $C_3$-$C_{10}$ cycloalkylene group, a substituted or unsubstituted $C_1$-$C_1$ heterocycloalkylene group, a substituted or unsubstituted phenylene group, a substituted or unsubstituted naphthylene group, *—O—*', *—C(═O)O—*', —OC(═O)—*', *—C(═O)NH—*', —NHC(═O)—*', or a combination thereof, a11 is an integer from 1 to 6, $A_{11}^-$ is a carboxylate anion, $B_{11}^+$is at least one of a substituted or unsubstituted sulfonium cation, a substituted or unsubstituted iodonium cation, or a substituted or unsubstituted ammonium cation, $A_{11}^-$ and $B_{11}^+$are linked via at least one of an ionic bond or a carbon-carbon covalent bond,

*and *' each indicate a binding site to a neighboring atom.

2. The polymer of claim 1, wherein $A_{11}^-$ is represented by Formula 2-2:

[Formula 2-2]

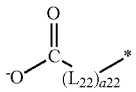

wherein, in Formulae 2-2, is at least one of a single bond, a $C_1$-$C_6$ alkylene group, a $C_1$-$C_6$ alkylene group substituted with fluorine (F), or a combination thereof, $a_{22}$ is an integer from 1 to 3, and

* indicates a binding site to a neighboring atom.

3. The polymer of claim 1, wherein $B_{11}^+$is represented by at least one of Formulae 3-1 to 3-3:

3-1

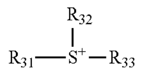

-continued 3-2

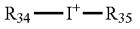

3-3

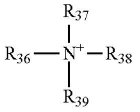

wherein, in Formulae 3-1 to 3-3, $R_{31}$ to $R_{39}$ are each independently at least one of a linear, branched, or cyclic $C_1$-$C_{20}$ monovalent hydrocarbon group that optionally includes a heteroatom, two adjacent groups among R31 to R33 are optionally bonded to each other to form a ring, R34 and R35 are optionally bonded to each other to form a ring, two adjacent groups among $R_{36}$ to $R_{39}$ are optionally bonded to each other to form a ring.

4. The polymer of claim 1, wherein $B_{11}{}^{+}$is represented by at least one of Formulae 3-11 to 3-13:

3-11

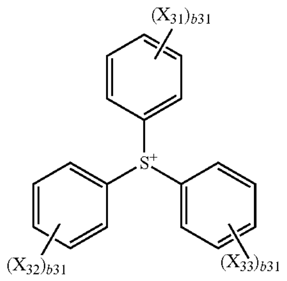

3-12

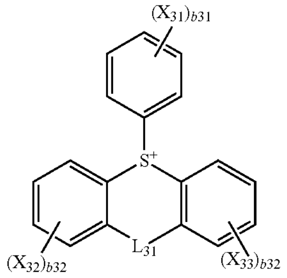

3-13

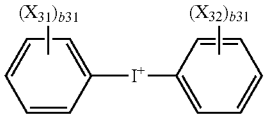

wherein, in Formulae 3-11 to 3-13, $X_{31}$ to $X_{33}$ are each independently at least one of hydrogen, a halogen, or a $C_1$-$C_6$ alkyl group, b31 is an integer from 1 to 5, b32 is an integer from 1 to 4, $L_{31}$ is at least one of a single bond, O, S, CO, SO, $SO_2$, CRR', or NR, and R and R' are each independently at least one of hydrogen, deuterium, a halogen, a hydroxyl group, a $C_1$-$C_6$ alkyl group, a $C_1$-$C_6$ alkoxy group, a $C_3$-$C_6$ cycloalkyl group, or a $C_3$-$C_6$ cycloalkoxy group.

5. The polymer of claim 1, further comprising:

a second repeating unit selected from at least one of the first repeating unit wherein $A_{11-}$ represented by Formula 2-1 or a repeating unit represented by at least one of Formula 4 or Formula 5:

Formula 2-1

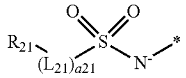

Formula 4

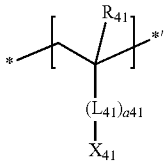

Formula 5

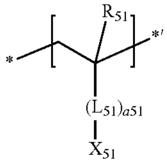

wherein, in Formula 2-1, $L_{21}$ is at least one of a single bond, a $C_1$-$C_6$ alkylene group, a $C_1$-$C_6$ alkylene group substituted with flourine (F), or a combination thereof, a21 is and integer from 1 to 3, and

* indicates a binding site to a neighboring atom, and wherein, in Formulae 4 and 5, $R_{41}$ and $R_51$ are each independently at least one of hydrogen, a halogen, $CH_3$, $CH_2F$, $CHF_2$, or $CF_3$, $L_{41}$ and $L_{51}$ are each independently at least one of a single bond, a substituted or unsubstituted $C_1$-$C_{10}$ alkylene group, a substituted or unsubstituted $C_3$-$C_1$i cycloalkylene group, a substituted or unsubstituted $C_3$-$C_1$ heterocycloalkylene group, a substituted or unsubstituted phenylene group, a substituted or unsubstituted naphthylene group, *—O—*', *—C(═O)O—*', —OC(═O)—*', *—C(═O)NH—*', —NHC(═O)—*', or a combination thereof, $a_{41}$ and $a_{51}$ are each independently an integer of 1 to 6, $X_{41}$ is an acid labile group, and $X_{51}$ is a non-acid labile group, and and *' each indicate a binding site to a neighboring atom.

6. The polymer of claim 5, wherein $X_{41}$ is represented by at least one of Formulae 6-1 to 6-7:

6-1

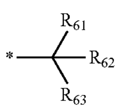

6-2

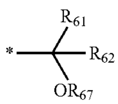

6-3

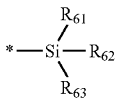

6-4

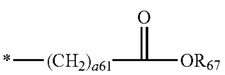

-continued 6-5

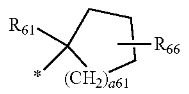

6-6

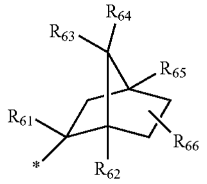

6-7

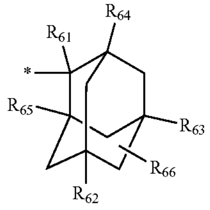

wherein, in Formulae 6-1 to 6-7, a61 is an integer from 0 to 6, $R_{61}$ to $R_{66}$ are each independently at least one of hydrogen or a linear, branched, or cyclic $C_1$-$C_{20}$ monovalent hydrocarbon group that optionally includes a heteroatom, $R_{67}$ is a linear, branched, or cyclic $C_1$-$C_{20}$ monovalent hydrocarbon group that optionally includes a heteroatom, two adjacent groups among $R_{61}$ to $R_{67}$ are optionally bonded to each other to form a ring, and indicates a binding site to a neighboring atom.

7. The polymer of claim 5, wherein $X_{51}$ is at least one of hydrogen or a linear, branched, or cyclic $C_1$-$C_{20}$ monovalent hydrocarbon group that includes one or more polar moieties, and the one or more polar moieties includes at least one of a hydroxy group, a halogen, a cyano group, a carbonyl group, a carboxyl group, *—O—*', *—C(=O)O—*', —OC(=O)—*', *—S(=O)O—*', —OS(=O)—*', a lactone ring, a sultone ring, or a carboxylic anhydride moiety.

8. The polymer of claim 5, wherein the repeating unit represented by Formula 4 is represented by at least one of Formulae 4-1 and 4-2:

4-1

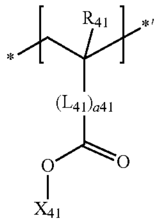

-continued 4-2

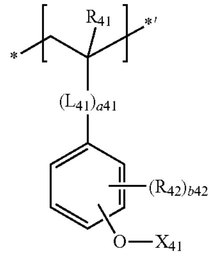

wherein, in Formulae 4-1 and 4-2, a41 is an integer from 1 to 4, $R_{42}$ is at least one of hydrogen or a linear, branched, or cyclic $C_1$-$C_{20}$ monovalent hydrocarbon group that optionally includes a heteroatom, b42 is an integer from 1 to 4, and

* and *' each indicate a binding site to a neighboring atom.

9. The polymer of claim 5, wherein the repeating unit represented by Formula 5 is represented by at least one of Formulae 5-1 and 5-2:

5-1

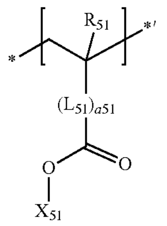

5-2

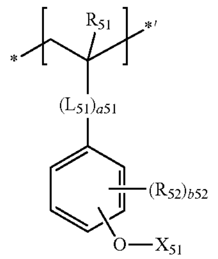

wherein, in Formulae 5-1 and 5-2, a51 is an integer from 1 to 4, $R_{52}$ is at least one of hydrogen, a hydroxyl group, or a linear, branched, or cyclic $C_1$-$C_{20}$ monovalent hydrocarbon group that optionally includes a heteroatom, b52 is an integer from 1 to 4, and

* and *' each indicate a binding site to a neighboring atom.

10. The polymer of claim 5, wherein an amount of the first repeating unit is in a range of about 1 mol % to about 60 mol %.

11. The polymer of claim 5, wherein the polymer includes both the repeating unit represented by Formula 4 and the repeating unit represented by Formula 5, an amount of the repeating unit represented by Formula 4 is in a range of about 1 mol % to about 60 mol % of the second repeating unit, and an amount of the repeating unit represented by Formula 5 is in a range of about 40 mol % to about 99 mol % of the second repeating unit.

12. The polymer of claim 1, wherein the polymer has a weight average molecular weight in a range of about 1,000 to about 500,000 and a polydispersity index (PDI: Mw/Mn) in a range of about 1.0 to about 3.0.

13. A photoresist composition comprising:

the polymer of claim 1;

an organic solvent;

a base resin; and a photoacid generator.

14. The photoresist composition of claim 13, wherein an amount of the polymer is in a range of about 0.1 parts by weight to about 40 parts by weight, based on 100 parts by weight of the base resin.

15. The photoresist composition of claim 13, wherein the base resin includes a repeating unit represented by Formula 4:

Formula 4

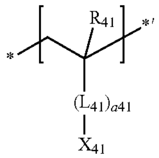

wherein, in Formula 4, $R_{41}$ is at least one of hydrogen, a halogen, $CH_3$, $CH_2F$, $CHF_2$, or $CF_3$, $L_{41}$ is at least one of a single bond, a substituted or unsubstituted $C_1$-$C_{10}$ alkylene group, a substituted or unsubstituted $C_3$-$C_{10}$ cycloalkylene group, a substituted or unsubstituted $C_3$-$C_{10}$ heterocycloalkylene group, a substituted or unsubstituted phenylene group, a substituted or unsubstituted naphthylene group, *—O—*', *—C(=O)O—*', —OC(=O)—*', *—C(=O)NH—*', —NHC(=O)—*', or a combination thereof, a41 is an integer from 1 to 6, $X_{41}$ is an acid labile group, and

* and *' each indicate a binding site to a neighboring atom.

16. The photoresist composition of claim 13, wherein the base resin further includes a repeating unit represented by Formula 5:

Formula 5

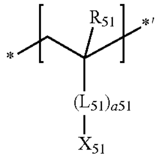

wherein, in Formula, $R_{51}$ is at least one of hydrogen, a halogen, $CH_3$, $CH_2F$, $CHF_2$, or $CF_3$, $L_{51}$ is at least one of a single bond, a substituted or unsubstituted $C_1$-$C_1$ alkylene group, a substituted or unsubstituted $C_3$—$C_{10}$ cycloalkylene group, a substituted or unsubstituted $C_3$-$C_{10}$ heterocycloalkylene group, a substituted or unsubstituted phenylene group, a substituted or unsubstituted naphthylene group, *—O—*', *—C(=O)O—*', —OC(=O)—*', *—C(=O)NH—*', —NHC(=O)—*', or a combination thereof, a51 is an integer from 1 to 6, $X_{51}$ is a non-acid labile group, and

* and *' each indicate a binding site to a neighboring atom.

17. The photoresist composition of claim 13, wherein the photoacid generator includes at least one of a sulfonium salt, an iodonium salt, or a combination thereof.

18. The photoresist composition of claim 13, wherein the photoacid generator is represented by Formula 7:

[Formula 7]

$$A_{71}^{+}B_{71}^{-}$$

wherein, in Formula 7, $A_{71}^{+}$is represented by Formula 7A, and $B_{71}^{-}$is represented by at least one of Formulae 7B to 7D, and $A_{71}^{+}$ and $B_{71}^{-}$are linked via at least one of an ion bond or a carbon-carbon covalent bond:

7A

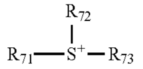

7B $$R_{74}—CF_2—SO_3^-$$

7C

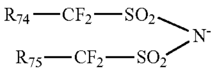

7D

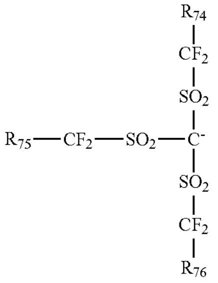

wherein, in Formulae 7 to 7D, $R_{71}$ to $R_{73}$ are each independently at least one of a linear, branched, or cyclic $C_1$-$C_{20}$ monovalent hydrocarbon group, two adjacent groups among $R_{71}$ to $R_{73}$ are optionally bonded to each other to form a ring, and $R_{74}$ to $R_{76}$ are each independently at least one of fluorine (F) or a linear, branched, or cyclic $C_1$-$C_{20}$ monovalent hydrocarbon group that optionally includes a heteroatom.

19. A method of forming a pattern, the method comprising:

forming a photoresist film by coating a board with the photoresist composition of claim 13;

exposing at least a portion of the photoresist film with high-energy rays; and developing the exposed photoresist film by applying a developing solution to the exposed photoresist film.

20. The method of claim 19, wherein the exposing is performed by irradiating at least one of a KrF excimer laser, an ArF excimer laser, extreme ultraviolet (EUV) rays, and/or an electron beam (EB).

* * * * *